(12) United States Patent  
Kim et al.

(10) Patent No.: US 9,488,575 B2  
(45) Date of Patent: Nov. 8, 2016

(54) MOBILE DEVICE WHICH SENSES PARTICULATE MATTER AND METHOD OF SENSING PARTICULATE MATTER WITH THE MOBILE DEVICE

(71) Applicant: SAMSUNG ELECTRONICS CO., LTD., Suwon-si (KR)

(72) Inventors: Jongseok Kim, Hwaseong-si (KR); Seokwhan Chung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/663,091

(22) Filed: Mar. 19, 2015

(65) Prior Publication Data

US 2016/0025628 A1    Jan. 28, 2016

(30) Foreign Application Priority Data

Jul. 24, 2014 (KR) .................. 10-2014-0094162

(51) Int. Cl.

| | | |
|---|---|---|
| *G01N 21/53* | (2006.01) | |
| *G01N 33/00* | (2006.01) | |
| *G01K 13/02* | (2006.01) | |
| *G01N 15/06* | (2006.01) | |

(52) U.S. Cl.
CPC ............. *G01N 21/53* (2013.01); *G01K 13/02* (2013.01); *G01N 33/004* (2013.01); *G01K 2013/024* (2013.01); *G01N 2015/0693* (2013.01); *G01N 2201/0221* (2013.01); *G01N 2201/066* (2013.01)

(58) Field of Classification Search
CPC .................................................... G01N 21/53
See application file for complete search history.

(56) References Cited

U.S. PATENT DOCUMENTS

| 8,578,756 B2 | 11/2013 | Suzuki |
| 8,677,803 B2 | 3/2014 | Hocken et al. |
| 2008/0087101 A1 | 4/2008 | Konstandopoulos |
| 2010/0044246 A1 | 2/2010 | Hall |
| 2011/0010071 A1 | 1/2011 | Rhodes et al. |
| 2011/0107815 A1 | 5/2011 | Nelson et al. |
| 2011/0215738 A1* | 9/2011 | Kamen ............... F03D 3/005 315/302 |
| 2011/0314796 A1 | 12/2011 | Nakamura et al. |
| 2012/0073267 A1 | 3/2012 | Cook et al. |
| 2012/0085146 A1 | 4/2012 | Maeda et al. |
| 2012/0119759 A1 | 5/2012 | Nelson et al. |
| 2012/0239308 A1 | 9/2012 | Miller et al. |
| 2012/0312074 A1 | 12/2012 | Allmendinger et al. |
| 2012/0324982 A1 | 12/2012 | Hocken et al. |
| 2013/0000678 A1 | 1/2013 | Hocken et al. |
| 2013/0038895 A1 | 2/2013 | Govyadinov et al. |

(Continued)

FOREIGN PATENT DOCUMENTS

| KR | 10-2006-0112725 A | 11/2006 |
| KR | 10-0797372 B1 | 1/2008 |

*Primary Examiner* — Tarifur Chowdhury  
*Assistant Examiner* — Omar Nixon  
(74) *Attorney, Agent, or Firm* — Sughrue Mion, PLLC

(57) ABSTRACT

A mobile device which senses particulate matter is provided. The mobile device includes a housing having an air flow path through which air flows when the mobile device is shaken; an inertia sensor that detects acceleration of the mobile device; a light-scattering type sensor that irradiates the air flow path with light and detects particulate matter in air flowing through the air flow path; and a controller that includes a counter for counting the particulate matter detected by the light-scattering type sensor, and a flow rate calculator for detecting an air flow rate of the air flow path based on a detection signal of the inertia sensor.

20 Claims, 13 Drawing Sheets

(56) References Cited

U.S. PATENT DOCUMENTS

| | | |
|---|---|---|
| 2013/0145821 A1 | 6/2013 | Lee et al. |
| 2013/0219990 A1 | 8/2013 | Allmendinger et al. |
| 2013/0222672 A1* | 8/2013 | Kim .................. H04N 5/23293 |
| | | 348/333.11 |
| 2013/0306840 A1* | 11/2013 | Kaletsch .................. G01T 7/00 |
| | | 250/208.1 |
| 2014/0227671 A1* | 8/2014 | Olmstead ............... G11B 27/10 |
| | | 434/308 |
| 2015/0241856 A1* | 8/2015 | Walser ................. F24F 11/0009 |
| | | 700/275 |

\* cited by examiner

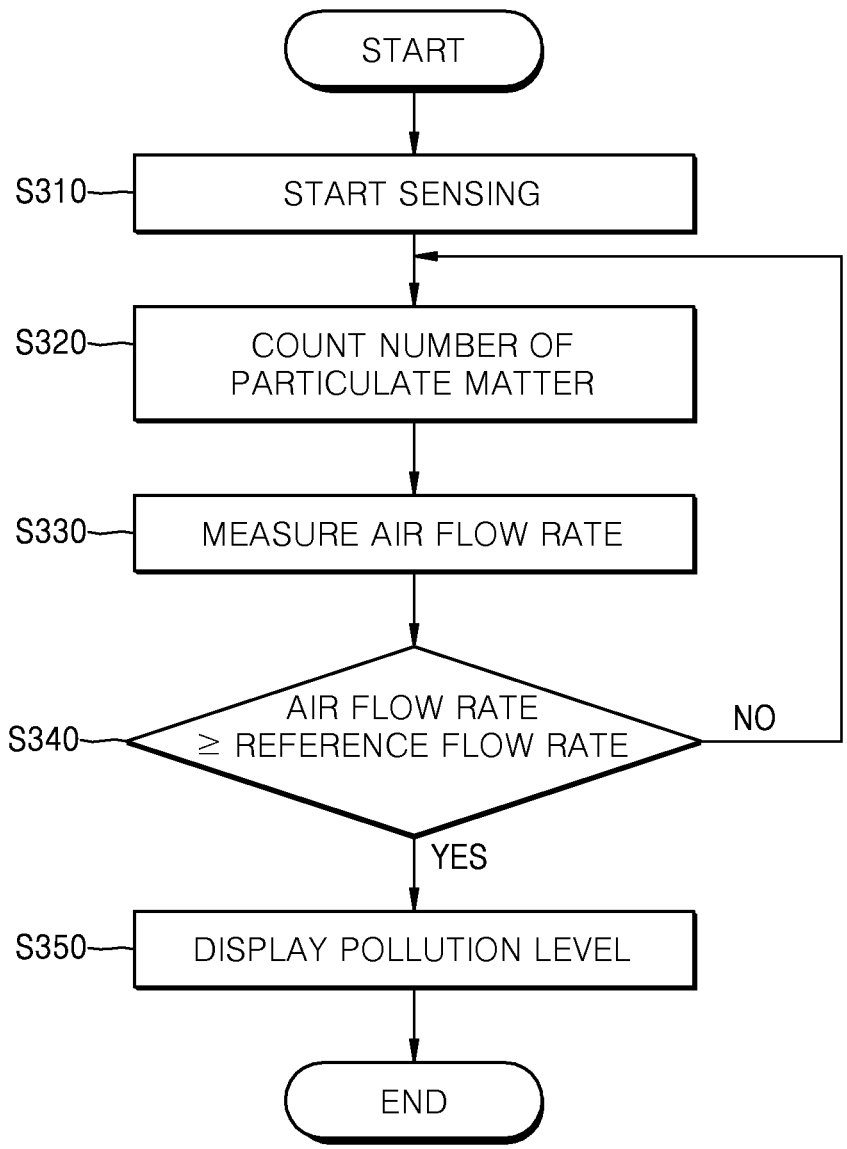

MOBILE DEVICE WHICH SENSES PARTICULATE MATTER AND METHOD OF SENSING PARTICULATE MATTER WITH THE MOBILE DEVICE

RELATED APPLICATION

This application claims priority from Korean Patent Application No. 10-2014-0094162, filed on Jul. 24, 2014, in the Korean Intellectual Property Office, the disclosure of which is incorporated herein in its entirety by reference.

BACKGROUND

1. Field

Methods and apparatuses consistent with the exemplary embodiments relate to a mobile device which detects particulate matter and a method of sensing the particulate matter.

2. Description of the Related Art

There is an increasing interest in particulate matter (PM) as a source of air pollution. Accordingly, requests to sense the PM by using small mobile devices are increasing.

PM sensors include a flow meter which induces an air flow and measures a flow rate, and a sensor which detects the PM. The sensor may be classified into, for example, a light-scattering type, a weight type, an electric signal type, and an inertial mass type, according to a detecting method.

In order to apply the PM sensor to a mobile device, the PM sensor has to be miniaturized. Additionally, components of the PM sensor have to be replaced periodically, in order to obtain an accurate sensed value. For example, a weight type sensor collects PM by passing air through a filter of the weight type sensor and senses an amount of the collected PM, but it is difficult to sense the amount in real-time since a collecting time is required, and the filter needs to be periodically replaced. An electric signal type sensor is applied to a diesel particulate filter (DPF) device of a car, wherein the electric signal type sensor only detects whether an amount of PM is equal to or higher than a reference amount, and requires an apparatus for removing PM on a sensing plate by using heat. An inertial mass type sensor transmits PM to a certain location and indirectly measures a weight of the sunken PM, wherein a quartz crystal microbalance (QCM) method is mainly used to measure the weight. A QCM needs to be periodically replaced. A light-scattering type sensor emits light on a sensing region where air passes through and collects light scattered by PM, wherein the light-scattering type sensor itself may be miniaturized, but a flow meter that supplies air and measures a flow rate has a relatively large size.

SUMMARY

Exemplary embodiments address at least the above problems and/or disadvantages and other disadvantages not described above. Also, the exemplary embodiments are not required to overcome the disadvantages described above, and an exemplary embodiment may not overcome any of the problems described above.

According to an aspect of the exemplary embodiments, there is provided a mobile device which has a miniaturized particulate matter sensing structure, and a method of sensing particulate matter.

Additional aspects will be set forth in part in the description which follows and, in part, will be apparent from the description, or may be learned by practice of the presented exemplary embodiments.

According to an aspect of the exemplary embodiments, a mobile device configured to sense particulate matter comprises a housing comprising an air flow path through which air flows when the mobile device is shaken; an inertia sensor configured to detect an acceleration of the mobile device; a light-scattering type sensor configured to irradiate the air flow path with light and detect particulate matter in air flowing through the air flow path; and a controller which comprises a counter configured to count the particulate matter detected by the light-scattering type sensor, and a flow rate calculator configured to detect an air flow rate of the air flow path based on a detection signal of the inertia sensor.

According to the exemplary embodiment, the mobile device may further include a temperature sensor configured to measure a temperature of the air, wherein the controller is configured to revise a density value of the air based on the measured temperature.

According to the exemplary embodiment, the housing may include a first opening and a second opening via which the air flow path communicates with an external region outside the housing.

According to the exemplary embodiment, the housing may further include an upper housing and a lower housing, wherein the first and second openings are respectively provided at the upper housing and the lower housing, and air flows through the air flow path when the mobile device is shaken in a thickness direction of the mobile device.

According to an aspect of the exemplary embodiment, the housing includes an upper housing, a lower housing, and a side housing connecting the upper and lower housing, wherein the first and second openings are respectively provided at two side walls of the side housing, the two side walls forming a corner, and air flows through the air flow path when the mobile device is shaken in a width direction of the mobile device.

According to the exemplary embodiment, the mobile device may further include a shutter configured to open or close the first and second openings. The mobile device may further include a switching sensor configured to detect whether the first and second openings are opened or closed by the shutter. When the switching sensor detects that the first and second openings are opened, the controller controls the mobile device to start sensing for the particulate matter.

According to the exemplary embodiment, the housing of the mobile device further include a shutter which is configured to move to a first location to open the first and second openings such that the air flow path communicates with the external region outside the housing, and to move to a second location to close the first and second openings such that a sensing region for sensing carbon dioxide (CO2) is formed, wherein the controller further includes a CO2 concentration calculator configured to calculate CO2 concentration based on an amount of light that passes through the sensing region and is detected by the light-scattering type sensor.

According to an aspect of the exemplary embodiment, the light-scattering type sensor may include a light-emitter configured to emit light and a light-receiver configured to receive light, wherein, when the shutter is at the first location, the light-receiver may receive light scattered by the particulate matter in the air flow path. The mobile device further includes a light path changing device configured to change a light path such that light that passes through the air flow path is not incident on the light-receiver when the shutter is at the first location.

According to the exemplary embodiment, when the shutter is at the second location, the light-receiver receives light that passes through the sensing region. The mobile device may further include a plurality of reflectors configured to guide light emitted from the light-emitter to be incident on the light-receiver after passing through the sensing region a plurality of times, when the shutter is at the second location.

According to another aspect of the exemplary embodiment, a method of sensing particulate matter with a mobile device comprises supplying air to an air flow path through a first opening and a second opening provided at a housing of the mobile device, by shaking the mobile device; detecting and counting particulate matter in the air flowing through the air flow path, with a light-scattering type sensor; detecting the acceleration of the mobile device with an inertia sensor, calculating the air flow rate based on the detected acceleration; outputting a pollution level calculated based on a count of the particulate matter when the calculated air flow rate reaches a reference flow rate, and stopping sensing of the particulate matter.

According to the exemplary embodiment, the supplying of the air to the air flow path may be performed when a detection signal of a switching sensor detects that the shutter is opened.

BRIEF DESCRIPTION OF THE DRAWINGS

These and/or other aspects will become apparent and more readily appreciated from the following description of the exemplary embodiments, taken in conjunction with the accompanying drawings in which:

FIG. 7 is a flowchart of a method of sensing a pollution level by particulate matter, according to an exemplary embodiment;

DETAILED DESCRIPTION OF EXEMPLARY EMBODIMENTS

Figure 1:
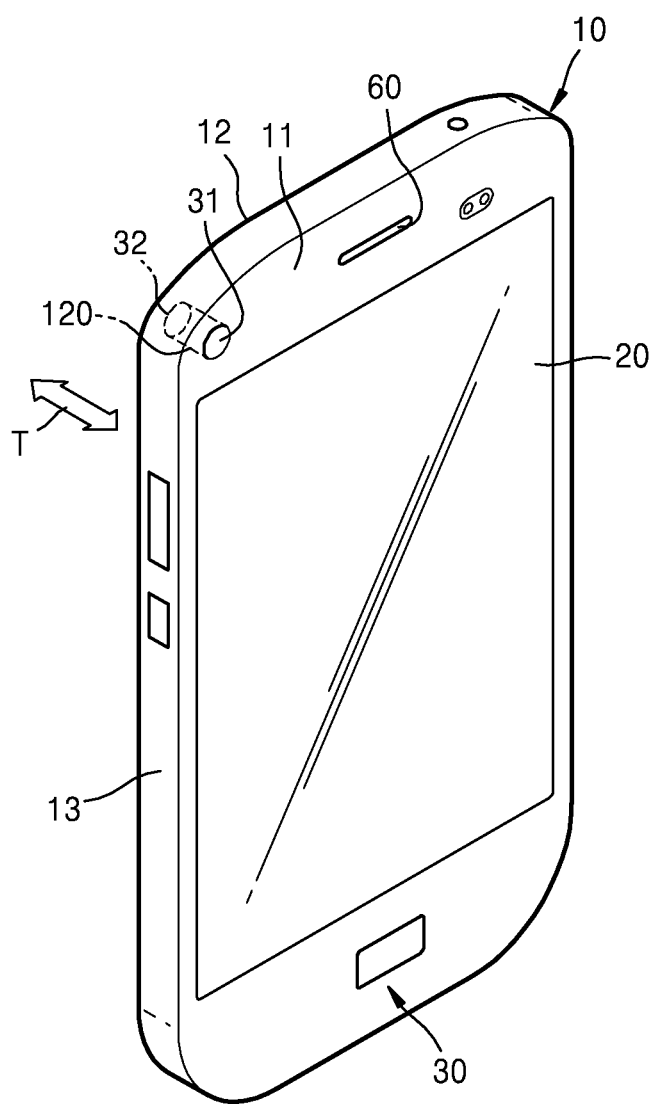
FIG. 1 is a plan view of a mobile device according to an exemplary embodiment.

Reference will now be made in detail to exemplary embodiments, examples of which are illustrated in the accompanying drawings, wherein like reference numerals refer to like elements throughout and sizes of components may be exaggerated for clarity. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items.

Figure 2:
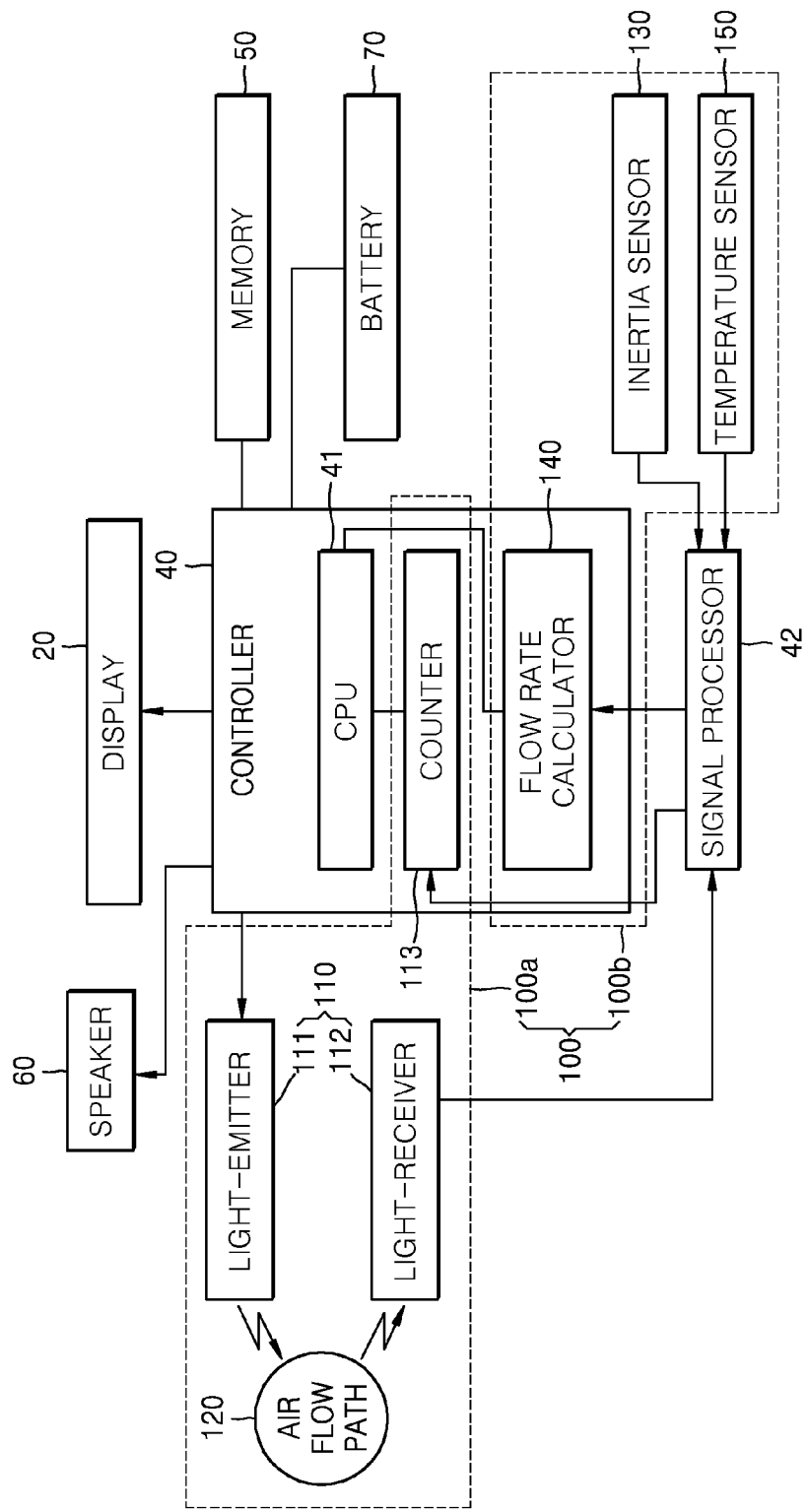
FIG. 2 is a block diagram of the mobile device of FIG. 1, according to an exemplary embodiment.
Figure 3:
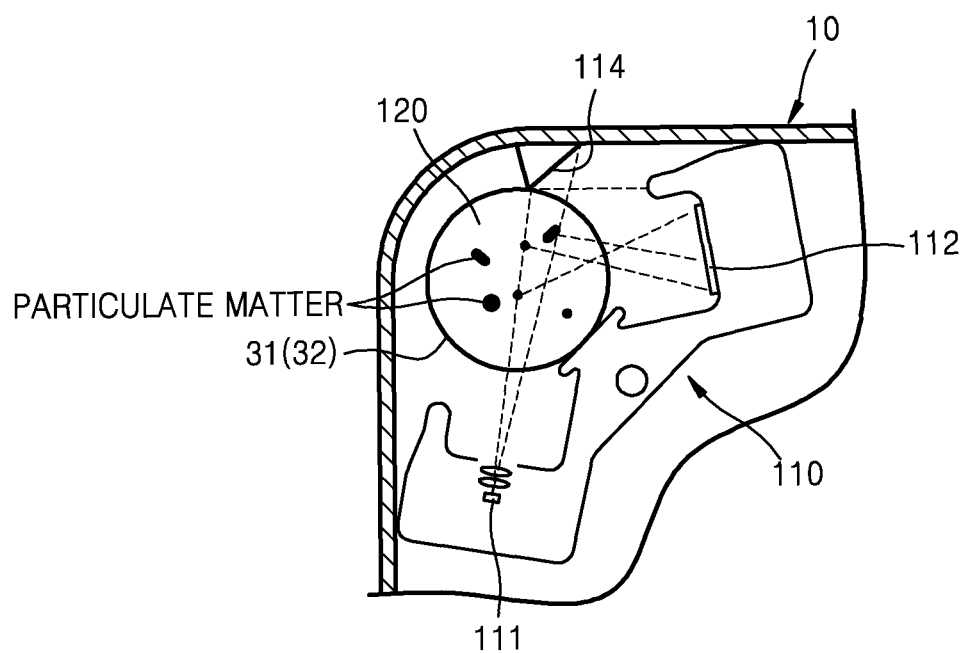
FIG. 3 is a plan view of a light-scattering type sensor applied to the mobile device of FIG. 1, according to an exemplary embodiment.

FIG. 1 is a plan view of a mobile device according to an exemplary embodiment. FIG. 2 is a block diagram of the mobile device of FIG. 1, according to an exemplary embodiment. FIG. 3 is a plan view of a light-scattering type sensor 110 applied to the mobile device of FIG. 1, according to an exemplary embodiment. Referring to FIGS. 1 through 3, a housing 10 of the mobile device and an apparatus 100 for sensing particulate matter are illustrated. The housing 10 may form an outer shape of the mobile device by including an upper housing 11, a lower housing 12, and a side housing 13 connecting the upper and lower housings 11 and 12, accommodate components forming the mobile devices therein, and support components exposed outside the housing 10.

The mobile device may include the apparatus 100 that senses particulate matter. In this case, the housing 10 forms an outer shape of the apparatus 100. A controller 40 performs functions for sensing particulate matter. The mobile device may include a display 20 as an image output device. The mobile device may include a speaker 60 as a sound output device. Also, the mobile device may include at least one button 30 as a manipulator.

The mobile device may be a portable device, such as a communication terminal, a game console, a multimedia device, a tablet computer, or a photographing apparatus, and may additionally have a function of sensing particulate matter. However, the type of mobile device is not limited thereto. The housing 10 may contain the controller 40 that performs functions according to a purpose of the mobile device, and an input and output device. If the mobile device is a multimedia terminal for viewing an image or listening to music, the controller 40 may include an image/sound information processor (not shown). If the mobile device is a mobile communication terminal, the controller 40 may include a communication module (not shown). The input and output device may include an image/sound input and output device and a manipulator (not shown) for user manipulation. The image input and output device may include, for example, the display 20. Also, the image input and output device may include a camera (not shown). The sound input and output device may be realized by, for example, the speaker 60 and a microphone (not shown). The manipulator may include the at least one button 30. The manipulator may be realized by a touch panel (not shown) integrated to the display 20. The controller 40 may be realized in, for example, a form of a circuit board including at least one central processing unit (CPU) 41. The controller 40 may execute software for driving the mobile device, which is stored in a memory 50, to operate the mobile device. A battery 70 supplies power for operating the mobile device.

The apparatus 100 may include a sensor 100*a* that senses particulate matter in air, and a flow meter 100*b* that provides air containing particulate matter to the sensor 100*a* and measures an air flow rate. The flow meter 100*b* may include a fan that induces an air flow, and a flow rate measurer that detects the air flow rate. However, a size of a flow meter including a fan may be too large to fit into the mobile device. Also, in order to drive the fan, power is supplied from the battery 70 of the mobile device. The use of the battery to provide power to the fan may increase the overall power consumption of the mobile device, and therefore reduces the overall operational time of the mobile device.

In this regard, the apparatus 100 according to the current exemplary embodiment uses an air flow induced by shaking the mobile device. Accordingly, referring to FIGS. 1 and 2, the housing 10 includes an air flow path 120. The air flow path 120 may communicate with external air via first and second openings 31 and 32 which face each other and respectively penetrate through the upper and lower housings 11 and 12. When the mobile device is shaken in a thickness direction T of the mobile device, air may flow from the first opening 31 to the second opening 32, and from the second opening 32, to the first opening 31.

The flow meter 100*b* may include an inertia sensor 130 that detects acceleration of the shaking mobile device, and a flow rate calculator 140 that calculates a flow rate based on an acceleration signal detected by the inertia sensor 130. A 3-dimensional (3D) acceleration signal of the inertia sensor 130 may be transmitted to the flow rate calculator 140 through, for example, a signal processor 42. The signal processor 42 may include an amplification circuit that amplifies a signal, and a noise filter circuit that removes noise from a signal. Also, as occasion demands, the signal processor 42 may include an analog-digital (AD) converter. An air flow rate of air passing through the air flow path 120 may be calculated by calculating a moved distance of the mobile device via a double integral of the acceleration signal, and multiplying a cross-sectional area A of the air flow path 120 by the calculated moved distance. In other words, when $v_x$ denotes a speed of the mobile device, $a_x$ denotes the acceleration of the mobile device, and $\Delta x$ denotes the moved distance of the mobile device during a period of time t, $\Delta x$ may be calculated according to Equation 1 below.

$$\Delta x = \int_{t}^{0} v_x(t')dt' = \int_{0}^{t}[\int_{0}^{t'} a_x(t'')dt'']dt' \qquad (1)$$

When Q denotes a volume flow rate of air that passed through the air flow path 120 during the period of time t, ρ denotes a density value of the air, and m denotes a mass flow rate of the air, Q and m may be calculated according to Equations 2 and 3 below.

$$Q = A \times \Delta x \qquad (2)$$

$$m = \rho \times Q \qquad (3)$$

The cross-sectional area A of the air flow path 120 may be a projected area in a thickness direction of the first and second openings 31 and 32.

As such, the flow meter 100*b* which does not include a fan may be realized. In order to increase accuracy of a mass flow rate, the flow meter 100*b* may further include a temperature sensor 150 that measures a temperature of the air. A detection signal of the temperature sensor 150 may be transmitted to the flow rate calculator 140 through the signal processor 42. The density value p of the air may be revised by using the measured temperature, thereby increasing accuracy of the mass flow rate. The flow rate calculator 140 may be realized in hardware, or realized in software driven by the CPU 41 of the mobile device. The flow rate calculator 140 may include a Kalman filter algorithm to increase accuracy of a flow rate.

When an inertia sensor is included in a mobile device, such as a communication terminal, a game console, a multimedia device, a tablet computer, or a photographing apparatus, there is no need to separately include the inertia sensor 130 for sensing particulate matter, and the flow meter 100*b* may measure a flow rate by using an acceleration signal of the inertia sensor which is already included in the mobile device.

The apparatus 100 according to the current exemplary embodiment employs a light-scattering type sensor as the sensor 100*a*. The light-scattering type sensor emits light to the air flow path 120 through which air passes, and counts a number of particulate matter by detecting the light scattered by the particulate matter included in the air. The light-scattering type sensor 1) may be satisfactorily maintained since a filter is not required to be replaced compared to a weight type sensor, 2) may quantitatively calculate an amount of particulate matter and may not use a heating apparatus for burning and removing particulate matter of a sensing apparatus compared to an electric signal type sensor, and 3) does not need to replace a quartz crystal microbalance (QCM) compared to an inertia mass type sensor. Also, the light-scattering type sensor has a relatively simple structure and may be miniaturized.

Referring to FIG. 3, the sensor 100*a* includes a light-emitter 111, a light-receiver 112, and a counter 113. The light-emitter 111 emits light to the air flow path 120 between the first and second openings 31 and 32. The light may be an infrared light. The light-emitter 111 may include a light source (not shown) and an optical unit (not shown), such as a lens, for guiding light emitted from the light source to the air flow path 120. The light-receiver 112 receives a light scattered by particulate matter included in the air passing through the air flow path 120. The light-receiver 112 may be realized by a linear or 2D photoelectric converter. The counter 113 counts the number of particulate matter in the air passing through the air flow path 120 based on a detection signal of the light-receiver 112. A reference numeral 114 denotes a light path changing unit that changes a light path such that the light which has passed through the air flow path 120 is not re-emitted to the light-receiver 112. Also, the light path changing unit 114 prevents the light which has passed through the air flow path 120 form being re-emitted to the air flow path 120. The light path changing unit 114 may be a reflecting unit that reflects a light in a direction other than the light-receiver 112 and the air flow path 120.

Figure 4:
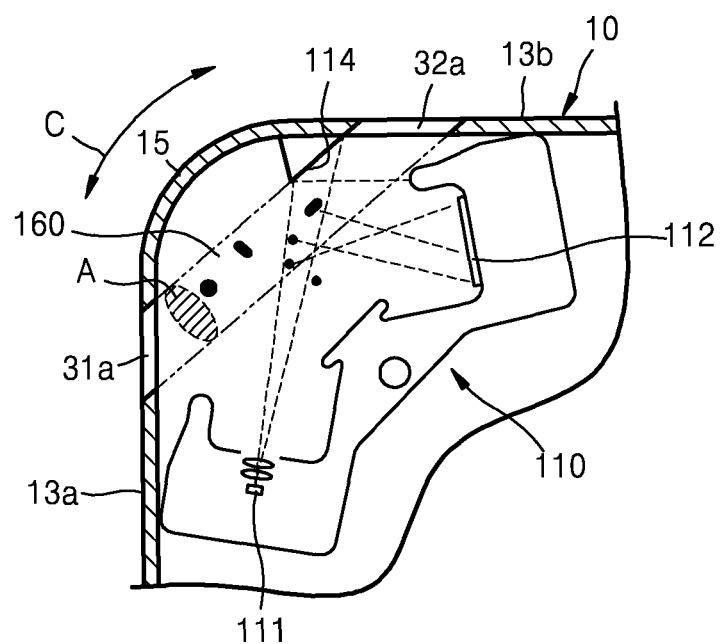
FIG. 4 is a schematic diagram of a mobile device showing an air flow path according to an exemplary embodiment.

However, a structure of the air flow path 120 is not limited to FIGS. 1 through 3. FIG. 4 is a schematic diagram of the mobile device showing the air flow path 120 according to an exemplary embodiment. Referring to FIG. 4, the mobile device according to the current exemplary embodiment may have a structure for inducing an air flow by shaking the mobile device in a width direction C. For example, first and second openings 31*a* and 32*a* may be formed respectively at two side walls 13*a* and 13*b* of the side housing 13, wherein the two side walls 13*a* and 13*b* form a corner 15. The air flow path 120 communicates with external air by the first and second openings 31*a* and 32*a*. Here, when the mobile device is shaken in the width direction C, air may flow from the first opening 31*a* to the second opening 32*a* and from the second opening 32*a* to the first opening 31*a*. The cross-sectional area A of the air flow path 120 is a cross-sectional area crossing an air flow direction at right angles. Referring to FIG. 4, in which the air flow path 120 is formed in the width direction C, since the first and second openings 31*a* and 32*a* are formed at sides of the mobile device, a style of an outer shape of the mobile device may not deteriorate. Also, even if the first and second openings 31*a* and 32*a* are formed larger than the first and second openings 31 and 32, the style of the outer shape is not affected, and thus an air flow rate of the air flow path 120 of FIG. 4 may be larger than that of FIG. 3.

Figure 5A:
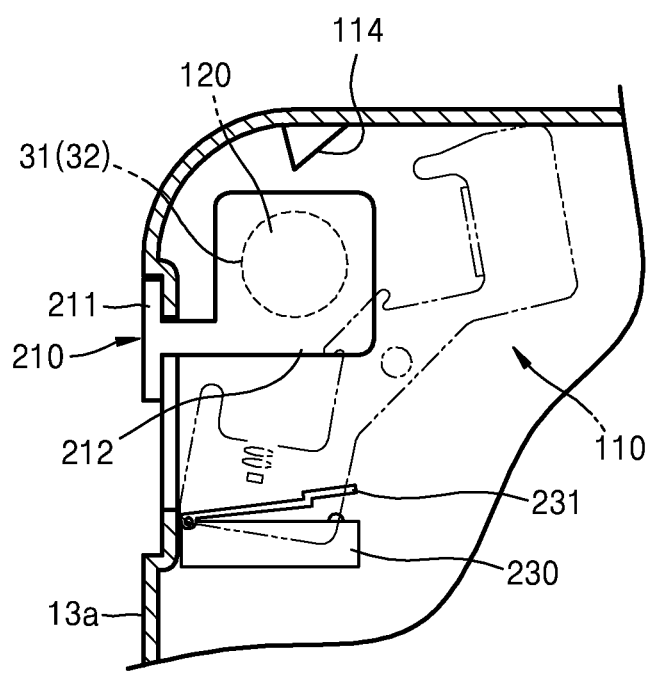
FIG. 5A is a schematic plan view of a shutter that opens or closes an air flow path of FIG. 3, wherein the shutter is closing an opening, according to an exemplary embodiment n.
Figure 5B:
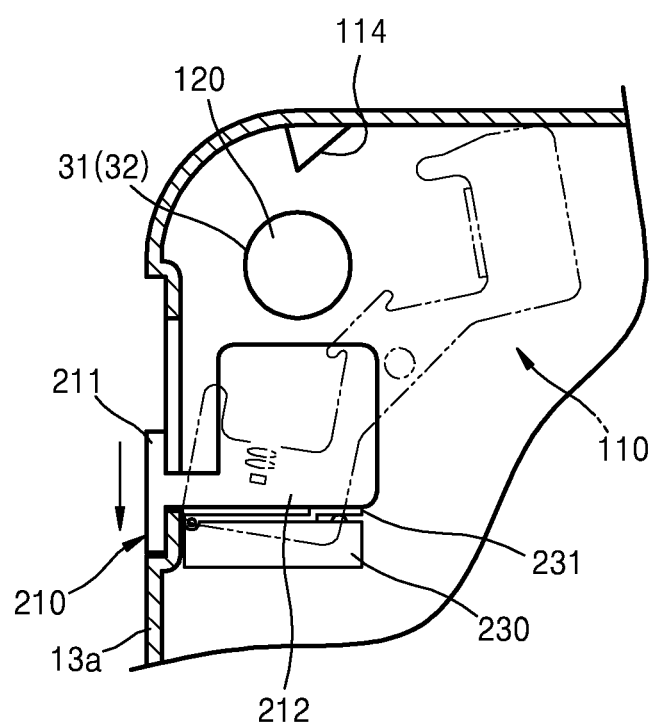
FIG. 5B is a schematic plan view of the shutter that opens or closes the air flow path of FIG. 3, wherein the shutter is opening the opening, according to an exemplary embodiment n.

FIGS. 5A and 5B are schematic plan views of a shutter 210 that opens or closes the air flow path 120 of FIG. 3. In FIG. 5A, the shutter 210 is closing the first and second openings 31 and 32, and in FIG. 5B, the shutter 210 is opening the first and second openings 31 and 32. Referring to FIGS. 5A and 5B, the shutter 210 that opens or closes the first and second openings 31 and 32 is illustrated. The shutter 210 is provided such that the shutter 210 is movable to a location (FIG. 5A) to close the first and second openings 31 and 32 and to a location (FIG. 5B) to open the first and second openings 31 and 32. For example, the shutter 210 is slidably provided at the side wall 13*a* of the housing 10. The shutter 210 includes a knob unit 211 exposed outside the side wall 13*a* to be manipulated by a user, and a shutter unit 212 connected to the knob unit 211. The shutter unit 212 may include two shutter panels spaced apart from each other in a thickness direction of the housing 10 and respectively closing or opening the first and second openings 31 and 32.

Accordingly, the first and second openings 31 and 32 may be closed when particulate matter is not sensed so that the light-emitter 111 or the light-receiver 112 is not contaminated by foreign substances transmitted into the housing 10 through the first and second openings 31 and 32, thereby maintaining reliability of sensing particulate matter. While sensing particulate matter, the shutter 210 may be slid to the location of FIG. 5B to open the first and second openings 31 and 32.

Figure 6A:
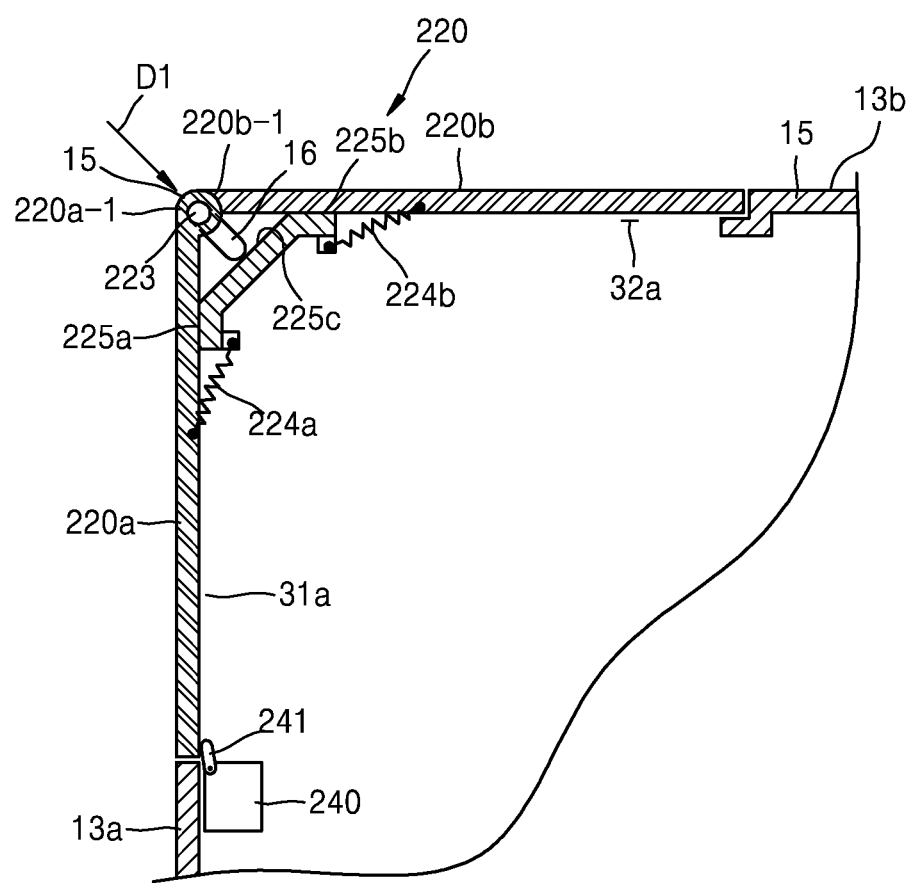
FIG. 6A is a schematic plan view of a shutter that opens or closes the air flow path of FIG. 4, wherein the shutter is closing an opening, according to an exemplary embodiment.
Figure 6B:
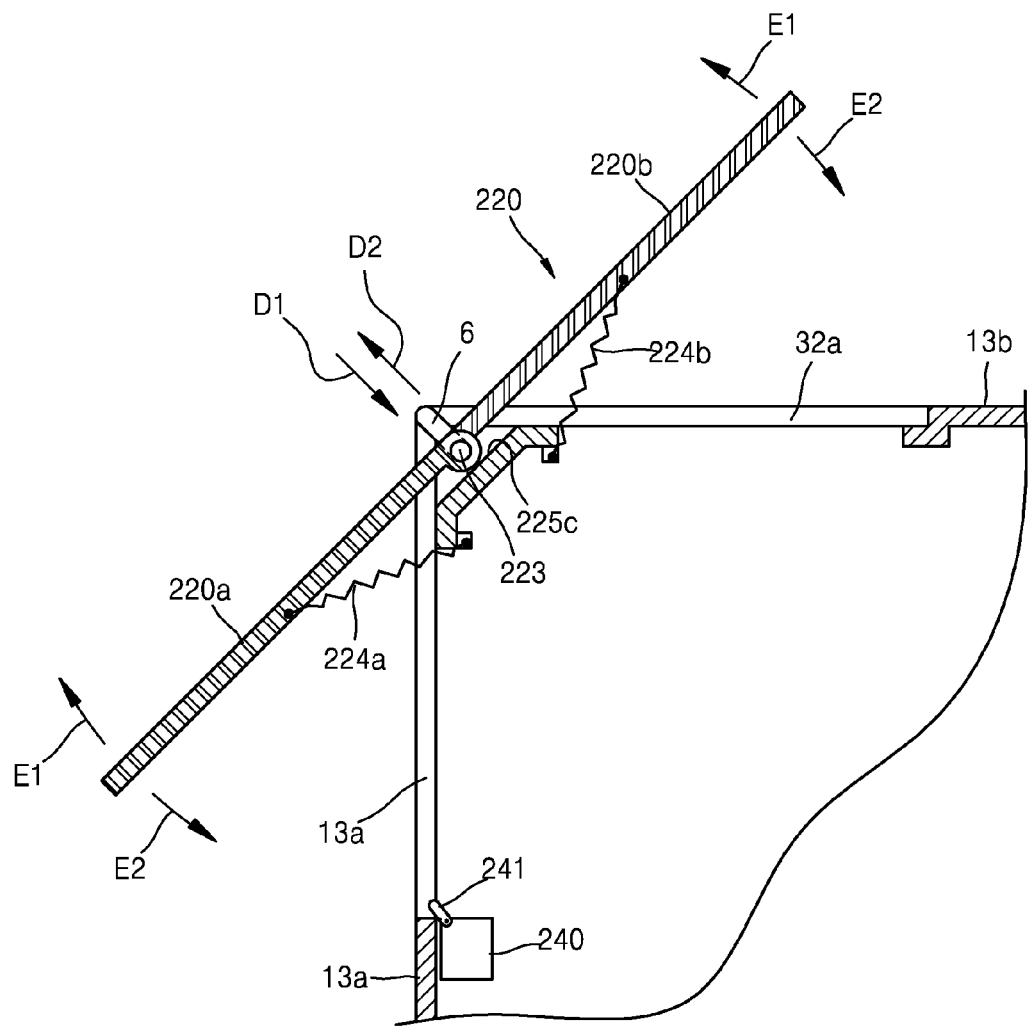
FIG. 6B is a schematic plan view of the shutter that opens or closes the air flow path of FIG. 4, wherein the shutter is opening the opening, according to an exemplary embodiment.

FIGS. 6A and 6B are schematic plan views of a shutter 220 that opens or closes the air flow path 120 of FIG. 4. In FIG. 6A, the shutter 220 is closing the first and second opening 31*a* and 32*a*, and in FIG. 6B, the shutter 220 is opening the first and second openings 31*a* and 32*a*. Referring to FIGS. 6A and 6B, the shutter 220 includes shutters 220*a* and 220*b* that are rotatably provided at a rotation shaft 223 located at the corner 15 formed by the side walls 13*a* and 13*b* where the first and second openings 31*a* and 32*a* are formed. The rotation shaft 223 is provided at the housing 10 to be movable in a diagonal direction of the mobile device from the corner 15. For example, the housing 10 may include a slot 16 that is cut in the diagonal direction to guide the rotation shaft 223. Elastic units 224*a* and 224*b* apply elastic force respectively to the shutters 220*a* and 220*b* in a direction rotating to close the first and second openings 31*a* and 32*a*. According to the current exemplary embodiment, an extension spring may be used as the elastic units 224*a* and 224*b*, but the elastic units 224*a* and 224*b* are not limited thereto. For example, the elastic units 224*a* and 224*b* may be torsion coil springs inserted into the rotation shaft 223.

In FIG. 6A, the shutters 220*a* and 220*b* are supported by first supports 225*a* and 225*b* to close the first and second openings 31*a* and 32*a*. At this time, when the rotation shaft 223 is pushed in a diagonal direction D1, one of ends 220*a*-1 and 220*b*-1 of the shutters 220*a* and 220*b* connected to the rotation shaft 223 move in the diagonal direction D1 along the slot 16. The shutters 220*a* and 220*b* are supported by a second support 225*c* having an angle with respect to the first supports 225*a* and 225*b*, and thus when the rotation shaft 223 moves in the diagonal direction D1 along the slot 16, the shutters 220*a* and 220*b* gradually rotate in a direction E1 indicated by an arrow, thereby opening the first and second openings 31*a* and 32*a* as shown in FIG. 6B. When the rotation shaft 223 moves in a direction D2 in FIG. 6B, the shutters 220*a* and 220*b* rotate in a direction E2 by elastic force of the elastic units 224*a* and 224*b*, and supported by the first supports 225*a* and 225*b* as shown in FIG. 6A, thereby closing the first and second openings 31*a* and 32*a*.

The rotation shaft 223 may be locked to the location of FIG. 6A and the location of FIG. 6B by a toggle unit (not shown). For example, when the rotation shaft 223 is pushed in the diagonal direction D1 in FIG. 6A, locking of the rotation shaft 223 is released and the rotation shaft 223 moves to the location of FIG. 6B. When the rotation shaft 223 reaches the location of FIG. 6B, the rotation shaft 223 is locked to the location of FIG. 6B by the toggle unit. Accordingly, the rotation shaft 223 is locked, and even if force of pushing the rotation shaft 223 is removed, the shutters 220*a* and 220*b* maintain opening the first and second openings 31*a* and 32*a*. When the rotation shaft 223 is pushed again in the diagonal direction D1 in FIG. 6B, the locking of the rotation shaft 223 is released and the rotation shaft 223 moves in the direction D2. When the rotation shaft 223 reaches the location of FIG. 6A, the rotation shaft 223 is locked to the location of FIG. 6A.

As shown in FIGS. 5A, 5B, 6A, and 6B, the mobile device may further include a switching sensor 230 or 240 for detecting opening and closing of the first and second openings 31 and 32 or 31*a* or 32*a*. The switching sensor 230 or 240 may be a micro-switch including an operation arm 231 or 241 pushed by the shutter 210 or 220. A detection signal of the switching sensor 230 or 240 is transmitted to the controller 40.

FIG. 7 is a flowchart of a method of sensing a pollution level based on particulate matter, according to an exemplary embodiment. A method of sensing particulate matter will be described with reference to the method of FIG. 7.

A sensing start switch, such as the button 30 of FIG. 1, may be pressed or an application program installed in the mobile device may be executed to start sensing particulate matter in operation S310. When the application program is executed, for example, a sensing start command may be input by touching a sensing start button on a user interface (UI) screen displayed on the display unit 20, thereby starting the sensing.

In FIGS. 5A, 5B, 6A, and 6B, the shutter 210 or 220 is activated to open the first and second openings 31 and 32 or 31*a* and 32*a* before starting the sensing. If the opening of the first and second openings 31 and 32 or 31*a* and 32*a* is not detected by the switching sensor 230 or 240, the controller 40 may output an alarm notifying closing of the first and second openings 31 and 32 or 31*a* and 32*a* to the display 20 and/or the speaker 60 via a visual signal and/or acoustic signal.

In FIGS. 5A, 5B, 6A, and 6B, the shutter 210 or 220 may operate as a sensing start switch. When opening of the first and second openings 31 and 32 or 31*a* or 32*a* is detected by the switching sensor 230 or 240, the controller 40 may control the mobile device to start the sensing.

Next, an air flow is generated through the first and second openings 31 and 32 or 31*a* or 32*a* by shaking the mobile device in the thickness direction T or the width direction C. Accordingly, air flows through the air flow path 120. When an acceleration signal detected by the inertia sensor 130 for a certain period of time after the sensing does not change nor has a change amount less than a reference amount, the controller 40 may output an alarm notifying a user to shake the mobile device. The reference amount may be pre-stored in the memory 50.

The controller 40 drives the light-emitter 111 to emit a light to the air flow path 120. The light-receiver 112 receives a light scattered by particulate matter, and transmits a light-receiving signal to the counter 113. The counter 113 counts the number of particulate matter based on the light-receiving signal in operation S320. The light that passed through the air flow path 120 is guided by the light path changing unit 114 such that the light is not re-emitted to the air flow path 120 and is not incident on the light-receiver 112.

A change of acceleration of the mobile device is continuously detected by the inertia sensor 130 when the mobile device is shaken, and an acceleration signal is transmitted to the flow rate calculator 140. The flow rate calculator 140 measures an air flow rate of the air flow path 120 according to Equations 1 through 3, in operation S330. The measured air flow rate is transmitted to the controller 40. The controller 40 may accurately calculate the air flow rate by revising the density p by using a temperature of air detected by the temperature sensor 150. For example, density data of air according to temperatures may be pre-stored in the memory 50, and the controller 40 may apply density of air corresponding to a detected temperature, which is read from the memory 50, to calculate an air flow rate.

The controller 40 continuously senses particulate matter until the air flow rate reaches a reference flow rate, in operation S340. The reference flow rate may be pre-stored in the memory 50. The controller 40 may compare the reference flow rate read from the memory 50 with the calculated air flow rate.

When the air flow rate reaches the reference flow rate, the controller 40 may generate a visual and/or acoustic alarm notifying that the sensing is ended. If the mobile device includes a vibrator, the controller 40 may drive the vibrator to output a tactile signal as an alarm. Upon recognizing an alarm, a user may stop shaking the mobile device.

The controller 40 may display a pollution level by using the number of detected particulate matter, in operation S350. For example, the pollution level may be visually displayed through the display 20. The number of particulate matter per the reference flow rate may be displayed as the pollution level. The controller 40 may output different acoustic signals through the speaker 60 based on whether the pollution level is lower than or higher than a reference pollution level stored in the memory 50.

As described above, a miniaturized flow meter without a fan may be realized by using the inertia sensor 130, and the apparatus 100 may be mounted on the mobile device. Also, if a portable communication terminal, such as a smart phone, includes the inertia sensor 130, an inertia sensor for sensing particulate matter is not separately required, and thus a mobile device which senses particulate matter may be realized at low costs. Also, the apparatus 100 may be miniaturized by using the light-scattering type sensor 110, and a pollution level by particulate matter may be relatively accurately measured in real-time.

Figure 8:
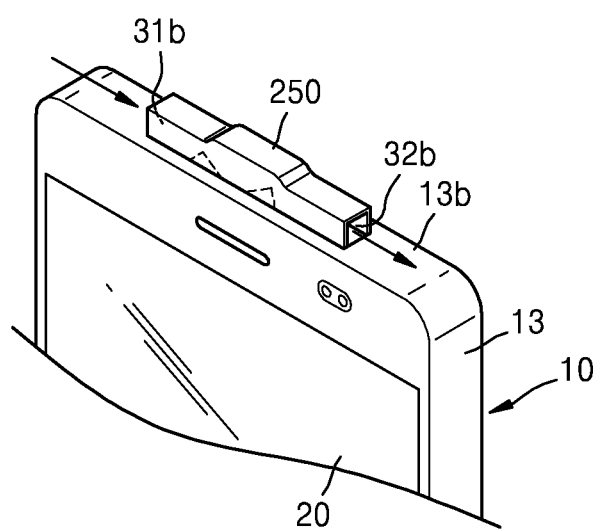
FIG. 8 is a partial perspective view of a mobile device according to an exemplary embodiment.
Figure 9:
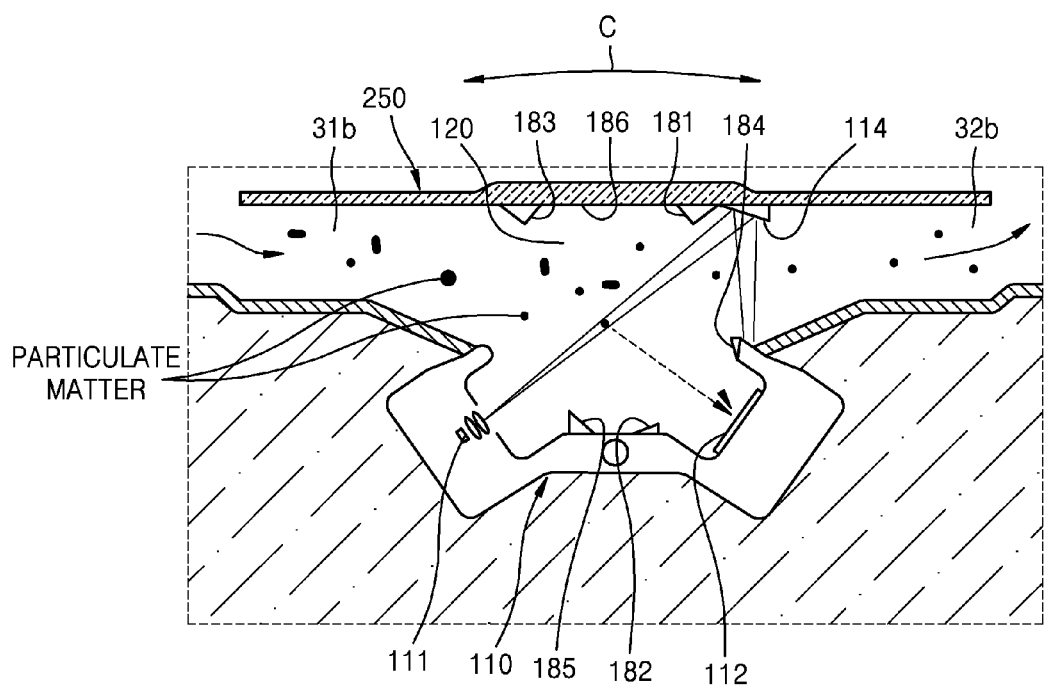
FIG. 9 is a schematic plan view of the mobile device of FIG. 8, wherein a shutter is opened, according to an exemplary embodiment.
Figure 10:
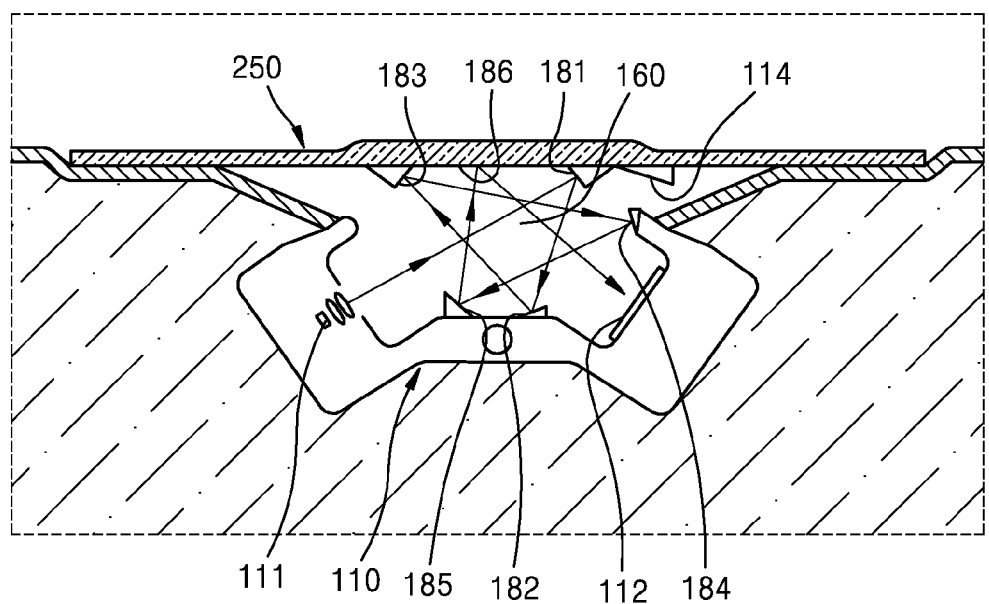
FIG. 10 is a schematic plan view of the mobile device of FIG. 8, wherein the shutter is closed, according to an exemplary embodiment.
Figure 11:
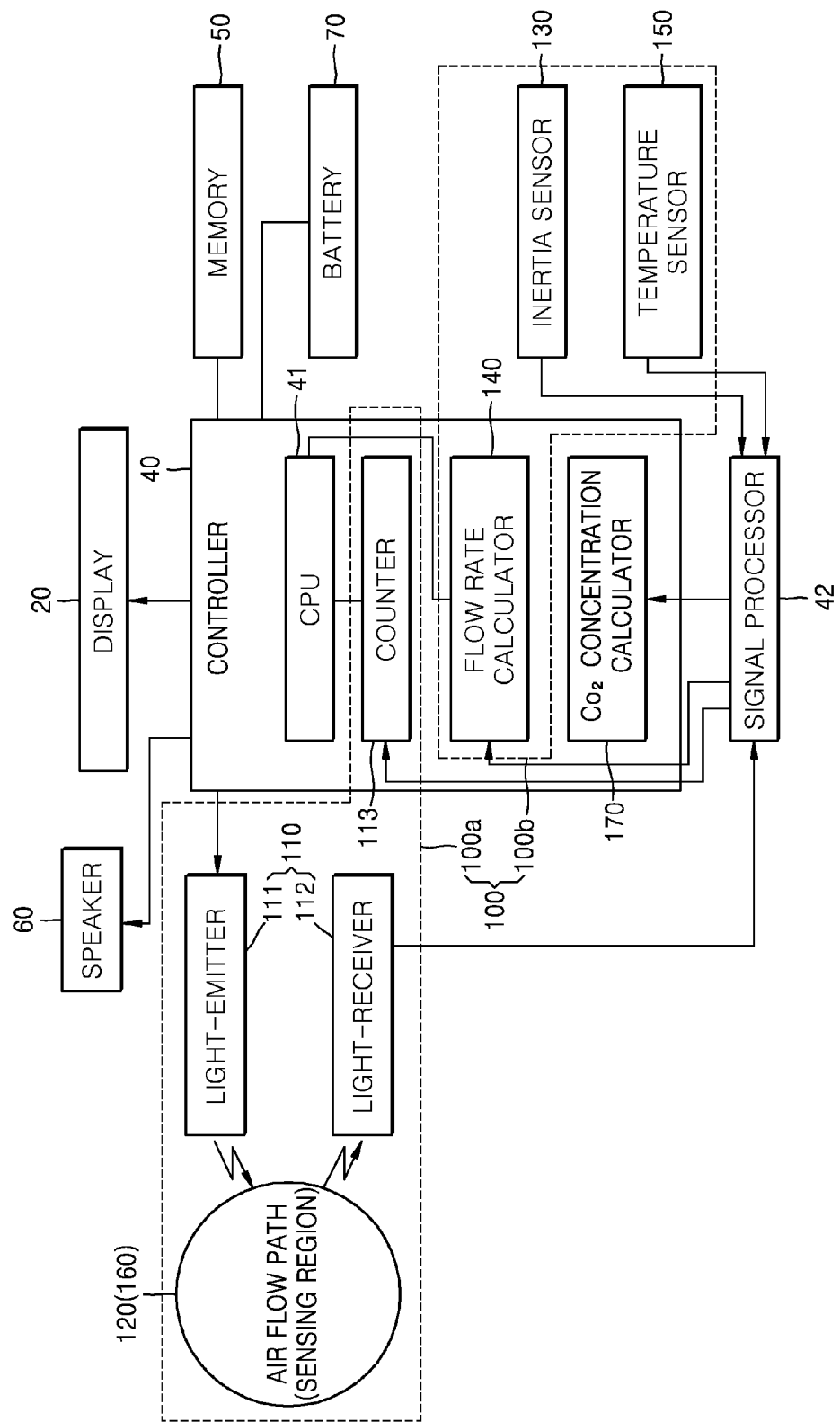
FIG. 11 is a bock diagram of the mobile device of FIG. 8, according to an exemplary embodiment.

FIG. 8 is a partial perspective view of a mobile device according to another exemplary embodiment. FIG. 9 is a schematic plan view of the mobile device of FIG. 8, wherein a shutter 250 is opened, according to an exemplary embodiment. FIG. 10 is a schematic plan view of the mobile device of FIG. 8, wherein the shutter 250 is closed, according to an exemplary embodiment. FIG. 11 is a bock diagram of the mobile device of FIG. 8, according to an exemplary embodiment.

The mobile device according to the current exemplary embodiment may sense particulate matter and sense the presence of carbon dioxide ($CO_2$). Referring to FIGS. 8 through 11, first and second openings 31b and 32b for communicating the air flow path 120/160 with external air may be provided at one side wall, for example, the side wall 13b of the side housing 13. The shutter 250 opens or closes the first and second openings 31b and 32b. In other words, the shutter 250 may move to a first location to open the first and second openings 31b and 32b such that external air flows through the air flow path 120, and to a second location to close the first and second openings 31b and 32b such that a sensing region 120/160 for sensing $CO_2$ is formed. As shown in FIG. 9, when the first and second openings 31b and 32b are opened by the shutter 250, particulate matter may be sensed, and as shown in FIG. 10, when the first and second openings 31b and 32b are closed by the shutter 250, $CO_2$ may be sensed.

For example, the shutter 250 may be connected to the housing 10 via a toggle unit (not shown). The shutter 250 may be locked to a location for closing the first and second openings 31b and 32b as shown in FIG. 10 by the toggle unit. At this time, when the shutter 250 is pressed, locking is released, and the shutter 250 may move and locked to a location for opening the first and second openings 31b and 32b as shown in FIG. 10. When the shutter 250 is pressed again, the shutter 250 may return back to the location shown in FIG. 9. How the shutter 250 is connected to the housing 10 such that the shutter 250 moves to the locations shown in FIGS. 9 and 10 is not limited.

First, referring to FIG. 9, in order to sense particulate matter, the shutter 250 is moved to the location for opening the first and second openings 31b and 32b. Then, external air flows through the air flow path 120 via the first and second openings 31b and 32b. At this time, when the mobile device is shaken in the width direction C, air may flow from the first opening 31b to the second opening 32b and from the second opening 32b to the first opening 31b. Light emitted from the light-emitter 111 is scattered by particulate matter and is detected by the light-receiver 112. The light path changing unit 114 changes a light path such that the light emitted from the light-emitter 111 is not incident on the light-receiver 112. The light path changing unit 114 is provided at the shutter 250, and when the shutter 250 opens the first and second openings 31b and 32b, reflects the light emitted from the light-emitter 111 such that the light is not incident on the light-receiving unit 112. As shown in FIG. 10, when the shutter 250 closes the first and second openings 31b and 32b, the light path changing unit 114 escapes from a light path for sensing $CO_2$, and a light is not incident on the light path changing unit 114. The counter 113 counts the number of particulate matter based on a detection signal detected by the light-receiver 112. The flow rate calculator 140 calculates an air flow rate of the air flow path 120 based on an acceleration signal of the mobile device detected by the inertia sensor 130. As described above, density of air may be revised by the temperature sensor 150. Since a method of sensing particulate matter has been described above with reference to FIGS. 1 through 7, details thereof are not repeated here.

Then, referring to FIGS. 10 and 11, the shutter 250 is at the location for closing the first and second openings 31b and 32b. At this time, the sensing region 160 for sensing $CO_2$ is formed in the housing 10. For example, when a $CO_2$ concentration sensing start command is input by pressing the button 30 or executing an application program installed in the mobile device, the controller 40 controls the light-emitter 111 to emit a light to the sensing region 160. A plurality of reflecting units 181 through 186 reflect a light emitted from the light-emitter 111 such that the light repeatedly passes through the sensing region 160. For example, in the current exemplary embodiment, the light passes through the sensing region 160 seven times, for example, by being reflected by the six reflecting units 181 through 186, but the exemplary embodiment is not limited thereto. At least the reflecting unit 181 from among the six reflecting units 181 through 186, which initially reflects the light emitted from the light-emitter 111 is provided at the shutter 250, and reflects the light to the sensing region 160 when the shutter 250 closes the first and second openings 31b and 32b, and is removed from a light path for sensing when the shutter 250 opens the first and second openings 31b and 32b. In the current exemplary embodiment, the reflecting units 181, 183, and 186 are disposed at the shutter 250.

CO2 has a certain absorption spectrum with respect to an infrared light. Accordingly, in the formula illustrated below, when "$I_0$" denotes an amount of infrared light emitted from the light-emitter 111, "I" denotes an amount of light penetrating through the sensing region 160, i.e., received by the light-receiver 112, "$\epsilon$" denotes an absorption rate of CO2, "c" denotes a concentration of CO2, and "l" denotes a length of an optical path passing through the sensing region 160, "I" may be calculated as follows.

$$I=I_0 e^{-\epsilon c l}$$

A light amount signal detected by the light-receiver 112 is transmitted to a CO2 concentration calculator 170 (FIG. 11) through the signal processor 42. The signal processor 42 may include an amplification circuit for amplifying a signal, and a noise filter circuit for removing noise from a signal. Also, as occasion demands, the signal processor 42 may include an A/D converter. The CO2 concentration calculator 170 may detect a concentration of CO2 by using a rating light amount (or the light output) of the light-emitter 111 and a received light amount of the light-receiver 112. The rating light amount ($I_0$) of the light-emitter 111, the absorption rate ($\epsilon$) of CO2, and the length (l) of the optical path may be stored in the memory 50. The CO2 concentration calculator 170 may be realized in hardware, or in software driven by the CPU 41 of the mobile device.

Generally, if a concentration of CO2 is lower than or equal to 700 ppm, a person may safely remain exposed to CO2 for an extended period of time. However, if the concentration of CO2 is about 1000 ppm, a person may experience unpleasant side effects as a result of the exposure to CO2, although there may be no damage to the person's health. If the concentration of CO2 is about 2000 ppm, a person may feel sleepy or drowsy, and the exposure may result in changes to the body of the person. If the concentration of CO2 is about 3000 ppm, a person may be harmed, for example, the person may feel stiffness in their shoulders or may have a headache. If the concentration of CO2 is equal to or greater than about 3000 ppm, a person may develop a headache or may feel dizziness. The controller 40 may visually output the concentration of CO2 through the display 20. Also, the controller 40 may output an alarm through the speaker 60 when the concentration of CO2 is, for example, equal to or higher than 1000 ppm.

Accordingly, a mobile device which senses particulate matter and which senses CO2 may be realized. Additionally, since the light-scattering type sensor 110 may be used to sense both particulate matter and CO2, the mobile device which senses particulate matter and CO2 may be miniaturized.

While one or more exemplary embodiments have been described with reference to the figures, it will be understood by those of ordinary skill in the art that various changes in form and details may be made therein without departing from the spirit and scope of the application as defined by the following claims.

What is claimed is:

1. A mobile device which senses particulate matter, the mobile device comprising:
    a housing configured to have an air flow path through which air flows in response to the mobile device being shaken;
    an inertia sensor configured to detect an acceleration of the mobile device;
    a light-scattering type sensor configured to irradiate the air flow path with light and detect particulate matter in air flowing through the air flow path; and
    a controller which comprises a counter configured to count the particulate matter detected by the light-scattering type sensor, and a flow rate calculator configured to detect an air flow rate of the air passing through the air flow path based on the acceleration of the mobile device detected by the inertia sensor.

2. The mobile device of claim 1, further comprising a temperature sensor configured to measure a temperature of the air, wherein the controller revises a density value of the air based on the measured temperature.

3. The mobile device of claim 1, wherein the housing comprises a first opening and a second opening through which the air flow path communicates with an external region outside the housing.

4. The mobile device of claim 3, wherein the housing comprises an upper housing and a lower housing, and
    wherein the first opening is provided at the upper housing and the second opening is provided at the lower housing, and air flows through the air flow path when the mobile device is shaken in a thickness direction of the mobile device.

5. The mobile device of claim 3, wherein the housing comprises an upper housing, a lower housing, and a side housing which connects the upper housing and the lower housing, and
    wherein the first opening and the second opening are respectively provided at two side walls of the side housing, the two side walls forming a corner, and air flows through the air flow path when the mobile device is shaken in a width direction of the mobile device.

6. The mobile device of claim 3, further comprising a shutter configured to open or close the first opening and the second opening.

7. The mobile device of claim 6, further comprising a switching sensor configured to detect whether the first opening and the second opening are opened or closed by the shutter.

8. The mobile device of claim 7, wherein, when the switching sensor is configured to detect that the first opening and the second opening are opened, the controller is configured to control the mobile device to start sensing for particulate matter.

9. The mobile device of claim 3, further comprising a shutter provided at the housing,
    wherein the shutter is movable to a first location to open the first opening and the second opening such that the air flow path communicates with the external region outside the housing, and to a second location to close the first opening and the second opening such that a sensing region for sensing carbon dioxide (CO2) is formed, and wherein the controller further comprises a CO2 concentration calculator configured to calculate CO2 concentration based on an amount of light that passes through the sensing region and is detected by the light-scattering type sensor.

10. The mobile device of claim 9, wherein the light-scattering type sensor comprises a light-emitter configured to emit light and a light-receiver configured to receive light, wherein, when the shutter is at the first location, the light-receiver receives light scattered by particulate matter in the air flow path.

11. The mobile device of claim 10, further comprising a light path changing unit configured to change a light path such that light that passes through the air flow path is not incident on the light-receiver when the shutter is at the first location.

12. The mobile device of claim 10, wherein, when the shutter is at the second location, the light-receiver receives light that passes through the sensing region.

13. The mobile device of claim 10, further comprising a plurality of reflecting units configured to guide light emitted from the light-emitter to be incident on the light-receiver after passing through the sensing region a plurality of times, when the shutter is at the second location.

14. A method of sensing particulate matter with a mobile device, the method comprising:

supplying air to an air flow path of the mobile device through a first opening and a second opening provided at a housing of the mobile device by shaking the mobile device;

detecting and counting particulate matter in air flowing through the air flow path, with a light-scattering type sensor;

detecting an acceleration of the mobile device with an inertia sensor, and calculating an air flow rate of the air passing through the air flow path based on the detected acceleration; and outputting a pollution level calculated based on a result of the counting of the particulate matter when the calculated air flow rate is equal to a reference flow rate, and stopping sensing of the particulate matter after the outputting of the pollution level.

15. The method of claim 14, wherein the supplying of the air is performed when a detection signal of a switching sensor which detects a location of a shutter which closes or opens the first opening and the second opening is received, and the shutter is detected to be open.

16. A mobile device which senses particulate matter and carbon dioxide, the mobile device comprising:

a housing configured to have an air flow path through which air flows;

a shutter configured to move to a first location to open the air flow path, and move to a second location to close the air flow path;

a light-scattering type sensor configured to irradiate the air flow path with light, and to detect particulate matter in air flowing in the air flow path when the shutter is located at the first location; and a carbon dioxide concentration calculator configured to control the light-scattering type sensor to irradiate the air flow path with light and to sense carbon dioxide in the air flow path based on the output of the light-scattering type sensor when the shutter is located at the second location.

17. The mobile device of claim 16, wherein the housing comprises a first opening and a second opening through which the air flow path communicates with an external region outside the housing.

18. The mobile device of claim 16, wherein the light-scattering type sensor comprises a light-emitter configured to emit light and a light-receiver configured to receive light.

19. The mobile device of claim 18, wherein the carbon dioxide concentration calculator detects a concentration of carbon dioxide based on a rating light amount of the light emitter and a received light amount of the light receiver.

20. The mobile device of claim 16, further comprising a light path changing unit configured to change a light path such that light that passes through the air flow path is not incident on the light-receiver when the shutter is at the first location.

* * * * *